(12) United States Patent
Adams et al.

(10) Patent No.: US 7,004,958 B2
(45) Date of Patent: Feb. 28, 2006

(54) TRANSVENOUS STAPLES, ASSEMBLY AND METHOD FOR MITRAL VALVE REPAIR

(75) Inventors: John M. Adams, Sammamish, WA (US); Scott J. Wolf, Bellevue, WA (US)

(73) Assignee: Cardiac Dimensions, Inc., Kirkland, WA (US)

( * ) Notice: Subject to any disclaimer, the term of this patent is extended or adjusted under 35 U.S.C. 154(b) by 609 days.

(21) Appl. No.: 10/093,323

(22) Filed: Mar. 6, 2002

(65) Prior Publication Data

US 2003/0171776 A1    Sep. 11, 2003

(51) Int. Cl.
*A61B 17/08* (2006.01)
(52) U.S. Cl. .................... 606/219; 606/151; 227/175.1
(58) Field of Classification Search ........ 606/139–157, 606/213–233
See application file for complete search history.

(56) References Cited

U.S. PATENT DOCUMENTS

| | | | |
|---|---|---|---|
| 4,055,861 A | 11/1977 | Carpentier et al. | |
| 4,164,046 A | 8/1979 | Cooley | |
| 4,485,816 A | 12/1984 | Krumme | |
| 4,550,870 A | 11/1985 | Krumme et al. | |
| 4,588,395 A | 5/1986 | Lemelson | |
| 4,830,023 A | 5/1989 | de Toledo et al. | |
| 5,061,277 A | 10/1991 | Carpentier et al. | |
| 5,250,071 A | 10/1993 | Palermo | |
| 5,261,916 A | 11/1993 | Engelson | |
| 5,265,601 A | 11/1993 | Mehra | |
| 5,350,420 A | 9/1994 | Cosgrove et al. | |
| 5,474,557 A * | 12/1995 | Mai ............................ | 606/78 |
| 5,514,161 A | 5/1996 | Limousin | |
| 5,554,177 A | 9/1996 | Kieval et al. | |
| 5,562,698 A | 10/1996 | Parker | |
| 5,584,867 A | 12/1996 | Limousin et al. | |
| 5,601,600 A | 2/1997 | Ton | |
| 5,676,671 A | 10/1997 | Inoue | |
| 5,733,325 A | 3/1998 | Robinson et al. | |
| 5,824,071 A | 10/1998 | Nelson et al. | |
| 5,891,193 A | 4/1999 | Robinson et al. | |
| 5,895,391 A | 4/1999 | Farnholtz | |

(Continued)

FOREIGN PATENT DOCUMENTS

EP        0893133 A1     1/1999

(Continued)

OTHER PUBLICATIONS

International Search Report for PCT/US03/06778 dated Aug. 5, 2003.

(Continued)

*Primary Examiner*—Glenn K. Dawson
(74) *Attorney, Agent, or Firm*—Wilson Sonsini Goodrich & Rosati (57) ABSTRACT

A mitral valve staple device treats mitral regurgitation of a heart. The device includes first and second leg portions, each leg portion terminating in a tissue piercing end, and a connection portion extending between the first and second leg portions. The connection portion has an initial stressed and distorted configuration to separate the first and second leg portion by a first distance when the tissue piercing ends pierce the mitral valve annulus and a final unstressed and undistorted configuration after the tissue piercing ends pierce the mitral valve annulus to separate the first and second leg portions by a second distance which is shorter than the first distance. The device is deployed within the heart transvenously through a catheter positioned in the coronary sinus adjacent the mitral valve annulus. A tool forces the mitral valve staple device through the wall of the catheter for deployment in the heart.

30 Claims, 4 Drawing Sheets

U.S. PATENT DOCUMENTS

| | | | |
|---|---|---|---|
| 5,899,882 | A | 5/1999 | Waksman et al. |
| 5,908,404 | A | 6/1999 | Elliott |
| 5,928,258 | A | 7/1999 | Khan et al. |
| 5,935,161 | A | 8/1999 | Robinson et al. |
| 5,961,545 | A | 10/1999 | Lentz et al. |
| 5,984,944 | A | 11/1999 | Forber |
| 6,027,517 | A | 2/2000 | Crocker et al. |
| 6,077,295 | A | 6/2000 | Limon et al. |
| 6,077,297 | A | 6/2000 | Robinson et al. |
| 6,096,064 | A | 8/2000 | Routh |
| 6,099,549 | A | 8/2000 | Bosma et al. |
| 6,099,552 | A | 8/2000 | Adams |
| 6,129,755 | A | 10/2000 | Mathis et al. |
| 6,171,320 | B1 | 1/2001 | Monassevitch |
| 6,190,406 | B1 | 2/2001 | Duerig et al. |
| 6,210,432 | B1 | 4/2001 | Solem et al. |
| 6,275,730 | B1 | 8/2001 | KenKnight et al. |
| 6,342,067 | B1 | 1/2002 | Mathis et al. |
| 6,352,553 | B1 | 3/2002 | van der Burg et al. |
| 6,352,561 | B1 | 3/2002 | Leopold et al. |
| 6,358,195 | B1 | 3/2002 | Green et al. |
| 6,395,017 | B1 | 5/2002 | Dwyer et al. |
| 6,402,781 | B1 | 6/2002 | Langberg et al. |
| 6,419,696 | B1 | 7/2002 | Ortiz et al. |
| 6,442,427 | B1 | 8/2002 | Boute et al. |
| 6,503,271 | B1 | 1/2003 | Duerig et al. |
| 6,537,314 | B1 | 3/2003 | Langberg et al. |
| 6,569,198 | B1 | 5/2003 | Wilson et al. |
| 6,589,208 | B1 | 7/2003 | Ewers et al. |
| 6,602,288 | B1 | 8/2003 | Cosgrove et al. |
| 6,602,289 | B1 | 8/2003 | Colvin et al. |
| 6,623,521 | B1 | 9/2003 | Steinke et al. |
| 6,626,899 | B1 | 9/2003 | Houser et al. |
| 6,797,001 | B1 | 9/2003 | Mathis et al. |
| 6,656,221 | B1 | 12/2003 | Taylor et al. |
| 6,716,158 | B1 | 4/2004 | Raman et al. |
| 6,718,985 | B1 | 4/2004 | Hlavka et al. |
| 6,723,038 | B1 | 4/2004 | Schroeder et al. |
| 6,764,510 | B1 | 7/2004 | Vidlund et al. |
| 6,776,784 | B1 * | 8/2004 | Ginn ..................... 606/151 |
| 6,793,673 | B1 | 10/2004 | Kowalsky et al. |
| 2001/0018611 | A1 | 8/2001 | Solem et al. |
| 2001/0044568 | A1 | 11/2001 | Langberg et al. |
| 2001/0049558 | A1 | 12/2001 | Liddicoat et al. |
| 2002/0016628 | A1 | 2/2002 | Langberg et al. |
| 2002/0035361 | A1 | 3/2002 | Houser et al. |
| 2002/0042621 | A1 | 4/2002 | Liddicoat et al. |
| 2002/0042651 | A1 | 4/2002 | Liddicoat et al. |
| 2002/0049468 | A1 | 4/2002 | Streeter et al. |
| 2002/0055774 | A1 | 5/2002 | Liddicoat |
| 2002/0065554 | A1 | 5/2002 | Streeter |
| 2002/0087173 | A1 | 7/2002 | Alferness et al. |
| 2002/0095167 | A1 | 7/2002 | Liddicoat et al. |
| 2002/0103532 | A1 | 8/2002 | Langberg et al. |
| 2002/0103533 | A1 | 8/2002 | Langberg et al. |
| 2002/0138044 | A1 | 9/2002 | Streeter et al. |
| 2002/0151961 | A1 | 10/2002 | Lashinski et al. |
| 2002/0169502 | A1 | 11/2002 | Mathis |
| 2002/0169504 | A1 | 11/2002 | Alferness et al. |
| 2002/0183835 | A1 | 12/2002 | Taylor et al. |
| 2002/0183836 | A1 | 12/2002 | Liddicoat et al. |
| 2002/0183837 | A1 | 12/2002 | Streeter et al. |
| 2002/0183838 | A1 | 12/2002 | Liddicoal et al. |
| 2002/0183841 | A1 | 12/2002 | Cohn et al. |
| 2003/0018358 | A1 | 1/2003 | Saadat |
| 2003/0069636 | A1 | 4/2003 | Solem et al. |
| 2003/0078465 | A1 | 4/2003 | Pai et al. |
| 2003/0078654 | A1 | 4/2003 | Taylor et al. |
| 2003/0083538 | A1 | 5/2003 | Adams et al. |
| 2003/0088305 | A1 | 5/2003 | Van Schie et al. |
| 2003/0105520 | A1 | 6/2003 | Alferness et al. |
| 2003/0130730 | A1 | 7/2003 | Cohn et al. |
| 2003/0130731 | A1 | 7/2003 | Vidlund et al. |
| 2003/0135267 | A1 | 7/2003 | Solem et al. |
| 2003/0144697 | A1 | 7/2003 | Mathis et al. |
| 2003/0171776 | A1 | 9/2003 | Adams et al. |
| 2003/0212453 | A1 | 11/2003 | Mathis et al. |
| 2004/0019377 | A1 | 1/2004 | Taylor et al. |
| 2004/0039443 | A1 | 2/2004 | Solem et al. |
| 2004/0073302 | A1 | 4/2004 | Rourke et al. |
| 2004/0098116 | A1 | 5/2004 | Callas et al. |
| 2004/0102839 | A1 | 5/2004 | Cohn et al. |
| 2004/0111095 | A1 | 6/2004 | Gordon et al. |
| 2004/0127982 | A1 | 7/2004 | Machold et al. |
| 2004/0133220 | A1 | 7/2004 | Lashinski et al. |
| 2004/0133240 | A1 | 7/2004 | Adams et al. |
| 2004/0133273 | A1 | 7/2004 | Cox |
| 2004/0138744 | A1 | 7/2004 | Lashinski et al. |
| 2004/0148019 | A1 | 7/2004 | Vidlund et al. |
| 2004/0148020 | A1 | 7/2004 | Vidlund et al. |
| 2004/0148021 | A1 | 7/2004 | Cartledge et al. |
| 2004/0153147 | A1 | 8/2004 | Mathis |
| 2004/0158321 | A1 | 8/2004 | Reuter et al. |
| 2004/0176840 | A1 | 9/2004 | Langberg |
| 2004/0193191 | A1 | 9/2004 | Starksen et al. |
| 2004/0193260 | A1 | 9/2004 | Alferness et al. |
| 2004/0220654 | A1 | 11/2004 | Mathis |
| 2004/0220657 | A1 | 11/2004 | Nieminen et al. |
| 2004/0243227 | A1 | 12/2004 | Starksen et al. |
| 2004/0243228 | A1 | 12/2004 | Kowalsky et al. |
| 2004/0249452 | A1 | 12/2004 | Adams et al. |
| 2004/0260342 | A1 * | 12/2004 | Vargas et al. ............... 606/219 |

FOREIGN PATENT DOCUMENTS

| | | |
|---|---|---|
| EP | 1050274 A1 | 11/2000 |
| EP | 1095634 A2 | 5/2001 |
| GB | 0741604 | 12/1955 |
| WO | WO 98/056435 A1 | 12/1998 |
| WO | WO 00/44313 A1 | 8/2000 |
| WO | WO 00/60995 | 10/2000 |
| WO | WO 01/00111 A1 | 1/2001 |
| WO | WO 01/50985 A1 | 7/2001 |
| WO | WO 01/54618 A1 | 8/2001 |
| WO | WO 01/87180 A2 | 11/2001 |
| WO | WO 02/00099 A2 | 1/2002 |
| WO | WO 02/01999 A2 | 1/2002 |
| WO | WO 02/05888 A1 | 1/2002 |
| WO | WO 02/19951 A1 | 3/2002 |
| WO | WO 02/34118 A2 | 5/2002 |
| WO | WO 02/47539 A2 | 6/2002 |
| WO | WO 02/053206 A2 | 7/2002 |
| WO | WO 02/62263 A2 | 8/2002 |
| WO | WO 02/62270 A1 | 8/2002 |
| WO | WO 02/62408 A2 | 8/2002 |
| WO | WO 02/76284 A2 | 10/2002 |
| WO | WO 02/78576 A2 | 10/2002 |
| WO | WO 02/96275 A2 | 12/2002 |
| WO | WO-03/15611 A2 | 2/2003 |
| WO | WO-03/49647 A1 | 6/2003 |
| WO | WO-03/59198 A2 | 7/2003 |
| WO | WO 03/063735 A2 | 8/2003 |
| WO | WO 04/045463 A2 | 6/2004 |
| WO | WO2004/084746 | 10/2004 |

OTHER PUBLICATIONS

International Search Report for PCT/US03/07022 dated Oct. 30, 2003.

Papageorgiou, P., et al., "Coronary Sinus Pacing Prevents Induction of Atrial Fibrillation," Circulation 96: 1893-1898, Sep. 16, 1977.

* cited by examiner

TRANSVENOUS STAPLES, ASSEMBLY AND METHOD FOR MITRAL VALVE REPAIR

FIELD OF THE INVENTION

The present invention generally relates to a device, assembly and method for treating dilated cardiomyopathy of a heart. The present invention more particularly relates to mitral valve annulus staple devices and an assembly and method for deploying such staple device to reshape the mitral valve annulus.

BACKGROUND OF THE INVENTION

The human heart generally includes four valves. Of these valves, a most critical one is known as the mitral valve. The mitral valve is located in the left atrial ventricular opening between the left atrium and left ventricle. The mitral valve is intended to prevent regurgitation of blood from the left ventricle into the left atrium when the left ventricle contracts. In preventing blood regurgitation the mitral valve must be able to withstand considerable back pressure as the left ventricle contracts.

The valve cusps of the mitral valve are anchored to muscular wall of the heart by delicate but strong fibrous cords in order to support the cusps during left ventricular contraction. In a healthy mitral valve, the geometry of the mitral valve ensures that the cusps overlie each other to preclude regurgitation of the blood during left ventricular contraction.

The normal functioning of the mitral valve in preventing regurgitation can be impaired by dilated cardiomyopathy caused by disease or certain natural defects. For example, certain diseases may cause dilation of the mitral valve annulus. This can result in deformation of the mitral valve geometry to cause ineffective closure of the mitral valve during left ventricular contraction. Such ineffective closure results in leakage through the mitral valve and regurgitation. Diseases such as bacterial inflammations of the heart or heart failure can cause the aforementioned distortion or dilation of the mitral valve annulus. Needless to say, mitral valve regurgitation must not go uncorrected.

One method of repairing a mitral valve having impaired function is to completely replace the valve. This method has been found to be particularly suitable for replacing a mitral valve when one of the cusps has been severely damaged or deformed. While the replacement of the entire valve eliminates the immediate problem associated with a dilated mitral valve annulus, presently available prosthetic heart valves do not possess the same durability as natural heart valves.

Various other surgical procedures have been developed to correct the deformation of the mitral valve annulus and thus retain the intact natural heart valve function. These surgical techniques involve repairing the shape of the dilated or deformed valve annulus. Such techniques, generally known as annuloplasty, require surgically restricting the valve annulus to minimize dilation. Here, a prosthesis is typically sutured about the base of the valve leaflets to reshape the valve annulus and restrict the movement of the valve annulus during the opening and closing of the mitral valve.

Many different types of prostheses have been developed for use in such surgery. In general, prostheses are annular or partially annular shaped members which fit about the base of the valve annulus. The annular or partially annular shaped members may be formed from a rigid material, such as a metal, or from a flexible material.

While the prior art methods mentioned above have been able to achieve some success in treating mitral regurgitation, they have not been without problems and potential adverse consequences. For example, these procedures require open heart surgery. Such procedures are expensive, are extremely invasive requiring considerable recovery time, and pose the concomitant mortality risks associated with such procedures. Moreover, such open heart procedures are particularly stressful on patients with a comprised cardiac condition. Given these factors, such procedures are often reserved as a last resort and hence are employed late in the mitral regurgitation progression. Further, the effectiveness of such procedures is difficult to assess during the procedure and may not be known until a much later time. Hence, the ability to make adjustments to or changes in the prostheses to obtain optimum effectiveness is extremely limited. Later corrections, if made at all, require still another open heart surgery.

An improved therapy to treat mitral regurgitation without resorting to open heart surgery has recently been proposed. This is rendered possible by the realization that the coronary sinus of a heart is near to and at least partially encircles the mitral valve annulus and then extends into a venous system including the great cardiac vein. As used herein, the term "coronary sinus" is meant to refer to not only the coronary sinus itself but in addition, the venous system associated with the coronary sinus including the great cardiac vein. The therapy contemplates the use of a device introduced into the coronary sinus to reshape and advantageously effect the geometry of the mitral valve annulus.

The device includes a resilient member having a cross sectional dimension for being received within the coronary sinus of the heart and a longitudinal dimension having an unstressed arched configuration when placed in the coronary sinus. The device partially encircles and exerts an inward pressure on the mitral valve. The inward pressure constricts the mitral valve annulus, or at least a portion of it, to essentially restore the mitral valve geometry. This promotes effective valve sealing action and eliminates mitral regurgitation.

The device may be implanted in the coronary sinus using only percutaneous techniques similar to the techniques used to implant cardiac leads such as pacemaker leads. One proposed system for implanting the device includes an elongated introducer configured for being releasably coupled to the device. The introducer is preferably flexible to permit it to advance the device into the heart and into the coronary sinus through the coronary sinus ostium. To promote guidance, an elongated sheath is first advanced into the coronary sinus. Then, the device and introducer are moved through a lumen of the sheath until the device is in position within the coronary sinus. Because the device is formed of resilient material, it conforms to the curvatures of the lumen as it is advanced through the sheath. The sheath is then partially retracted to permit the device to assume its unstressed arched configuration. Once the device is properly positioned, the introducer is then decoupled from the device and retracted through the sheath. The procedure is then completed by the retraction of the sheath. As a result, the device is left within the coronary sinus to exert the inward pressure on the mitral valve to restore mitral valve geometry.

The foregoing therapy has many advantages over the traditional open heart surgery approach. Since the device, system and method may be employed in a comparatively noninvasive procedure, mitral valve regurgitation may be treated at an early stage in the mitral regurgitation progression. Further, the device may be placed with relative ease by any minimally invasive cardiologist. Still further, since the heart remains completely intact throughout the procedure, the effectiveness of the procedure may be readily determined. Moreover, should adjustments be deemed desirable, such adjustments may be made during the procedure and before the patient is sent to recovery.

Another approach to treat mitral regurgitation with a device in the coronary sinus is based upon the observation that the application of a localized force against a discrete portion of the mitral valve annulus can terminate mitral regurgitation. This suggests that mitral regurgitation may be localized and nonuniform. Hence, the device applies a force to one or more discrete portions of the atrial wall of the coronary sinus to provide localized mitral valve annulus reshaping instead of generalized reshaping of the mitral valve annulus. Such localized therapy would have all the benefits of the generalized therapy. In addition, a localized therapy device may be easier to implant and adjust.

A still further approach to treat mitral regurgitation from the coronary sinus of the heart contemplates a device having a first anchor configured to be positioned within and fixed to the coronary sinus of the heart adjacent the mitral valve annulus within the heart, a cable fixed to the first anchor and extending proximally from the first anchor within the heart, a second anchor configured to be positioned in and fixed in the heart proximal to the first anchor and arranged to slidingly receive the cable, and a lock that locks the cable on the second anchor. When the first and second anchors are fixed within the heart, the cable may be drawn proximally and locked on the second anchor. The geometry of the mitral valve is thereby effected. This approach provides flexibility in that the second anchor may be positioned and fixed in the coronary sinus or alternatively, the second anchor may be positioned and fixed in the right atrium. This approach further allows adjustments in the cable tension after implant.

A still further alternative for treating mitral regurgitation contemplates a device having a first anchor configured to be positioned within and anchored to the coronary sinus of the heart adjacent the mitral valve annulus within the heart. A second anchor is configured to be positioned within the heart proximal to the first anchor and adjacent the mitral valve annulus within the heart. A connecting member, having a fixed length, is permanently attached to the first and second anchors. As a result, when the first and second anchors are within the heart with the first anchor anchored in the coronary sinus, the second anchor may be displaced proximally to effect the geometry of the mitral valve annulus and released to maintain the effect on the mitral valve geometry. The second anchor may be configured, when deployed, to anchor against distal movement but be moveable proximally to permit the second anchor to be displaced proximally within the coronary sinus. The present invention provides a still further approach for treating mitral regurgitation.

SUMMARY OF THE INVENTION

The invention provides a device for effecting tissue geometry of an organ. The device includes first and second leg portions, each leg portion terminating in a tissue piercing end, and a connection portion extending between the first and second leg portions, the connection portion having an initial stressed and distorted configuration to separate the first and second leg portions by a first distance when the tissue piercing ends pierce the tissue and a final unstressed and undistorted configuration after the tissue piercing ends pierce the tissue to separate the first and second leg portions by a second distance, the second distance being shorter than the first distance.

The present invention further provides a device for effecting mitral valve annulus geometry of a heart. The device includes first and second leg portions, each leg portion terminating in a tissue piercing end, and a connection portion extending between the first and second leg portions. The connection portion has an initial stressed and distorted configuration to separate the first and second leg portions by a first distance when the tissue piercing ends pierce the mitral valve annulus and a final unstressed and undistorted configuration after the tissue piercing ends pierce the mitral valve annulus to separate the first and second leg portions by a second distance, the second distance being shorter than the first distance.

The initial configuration of the connection portion may be a first arched configuration and the final configuration of the connection portion may be a second arched configuration, wherein the second arched configuration is arched in a direction opposite the first arched configuration. The device may be configured such that when the connection portion is in the second arched configuration, the tissue piercing ends of the leg portions point toward each other. The leg portions and connection portion are preferably formed of the same material stock, as from Nitinol, for example.

The invention further provides a device for effecting mitral valve annulus geometry of a heart. The device includes first and second tissue piercing portions, each tissue piercing portion terminating in a tissue piercing end, and a connection portion extending between the first and second tissue piercing portions, the connection portion having an initial stressed and distorted configuration to separate the first and second tissue piercing portions by a first distance when the tissue piercing ends pierce the mitral valve annulus and a final unstressed and undistorted configuration after the tissue piercing ends pierce the mitral valve annulus to separate the first and second tissue piercing portions by a second distance, the second distance being shorter than the first distance.

The invention further provides an assembly for effecting mitral valve annulus geometry of a heart. The assembly includes an elongated catheter being placeable in the coronary sinus of the heart adjacent the mitral valve annulus. The assembly further includes at least one staple carried within the catheter, the at least one staple including first and second leg portions, each leg portion terminating in a tissue piercing end, and a connection portion extending between the first and second leg portions, the connection portion having an initial stressed and distorted configuration to separate the first and second leg portions by a first distance when the tissue piercing ends pierce the mitral valve annulus and a final unstressed and undistorted configuration after the tissue piercing ends pierce the mitral valve annulus to separate the first and second leg portions by a second distance, the second distance being shorter than the first distance. The assembly further includes a tool that forces the at least one staple from the catheter to cause the tissue piercing ends of the first and second leg portions of the at least one staple to pierce the mitral valve annulus with the connection portion of the at least one staple in the initial configuration.

The at least one staple is preferably configured so that the tissue piercing ends of the first and second leg portions point away from each other when the connection portion is in the initial configuration and the tissue piercing ends of the first and second leg portions point toward each other when the connection portion is in the final configuration.

The catheter preferably includes a tubular wall wherein the tool forces the at least one staple through the tubular wall of the catheter. To that end, the tubular wall may include a break-away slot adjacent the at least one staple that permits the at least one staple to be forced therethrough.

The at least one staple may comprise a plurality of staples. The catheter tubular wall may in turn include a plurality of break-away slots, each slot being adjacent to a respective given one of the staples, the slots permitting the staples to be forced through the tubular wall of the catheter and into the mitral valve annulus. The tool is preferably configured to force the plurality of staples from the catheter substantially simultaneously.

The assembly may further include an urging member that urges the catheter along and against a wall of the coronary sinus adjacent to the mitral valve annulus. The urging member may be an elongated balloon carried by the catheter.

The invention still further provides a method of effecting mitral valve annulus geometry of a heart. The method includes the steps of providing at least one staple including first and second leg portions, each leg portion terminating in a tissue piercing end, and a connection portion extending between the first and second leg portions, the connection portion having an initial stressed and distorted configuration to separate the first and second leg portions by a first distance when the tissue piercing ends pierce the mitral valve annulus and a final unstressed and undistorted configuration after the tissue piercing ends pierce the mitral valve annulus to separate the first and second leg portions by a second distance, the second distance being shorter than the first distance, placing the at least one staple into a catheter, and locating the catheter in the coronary sinus of the heart so that the at least one staple is adjacent the mitral valve annulus. The method includes the further step of releasing the at least one staple from the catheter to cause the tissue piercing ends of the first and second leg portions of the at least one staple to pierce the mitral valve annulus with the connection portion of the at least one staple in the initial configuration and causing the connection portion to assume the final configuration.

The invention still further provides an assembly for effecting mitral valve annulus geometry of a heart. The assembly includes

BRIEF DESCRIPTION OF THE DRAWINGS

The features of the present invention which are believed to be novel are set forth with particularity in the appended claims. The invention, together with further aspects and advantages thereof, may best be understood by making reference to the following description taken in conjunction with the accompanying drawings, in the several figures of which like reference numerals identify identical elements, and wherein:

DETAILED DESCRIPTION OF THE INVENTION

Figure 1:
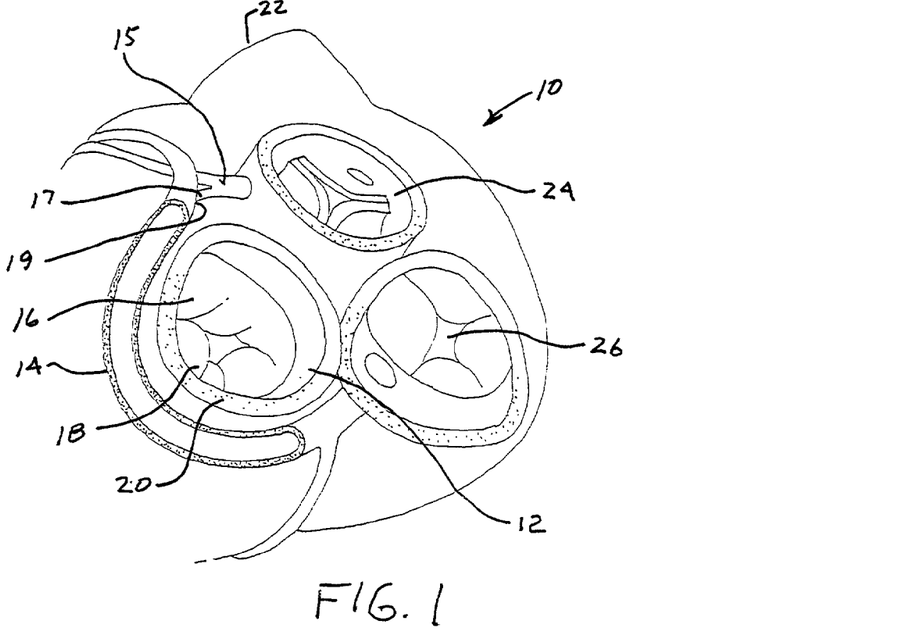
FIG. 1 is a superior view of a human heart with the atria removed.

Referring now to FIG. 1, it is a superior view of a human heart 10 with the atria removed to expose the mitral valve 12, the coronary sinus 14, the coronary artery 15, and the circumflex artery 17 of the heart 10 to lend a better understanding of the present invention. Also generally shown in FIG. 1 are the pulmonary valve 22, the aortic valve 24, and the tricuspid valve 26 of the heart 10.

The mitral valve 12 includes an anterior cusp 16, a posterior cusp 18 and an annulus 20. The annulus encircles the cusps 16 and 18 and maintains their spacing to provide a complete closure during a left ventricular contraction. As is well known, the coronary sinus 14 partially encircles the mitral valve 12 adjacent to the mitral valve annulus 20. As is also known, the coronary sinus is part of the venus system of the heart and extends along the AV groove between the left atrium and the left ventricle. This places the coronary sinus essentially within the same plane as the mitral valve annulus making the coronary sinus available for placement of the mitral valve therapy staple devices of the present invention therein.

Figure 2:
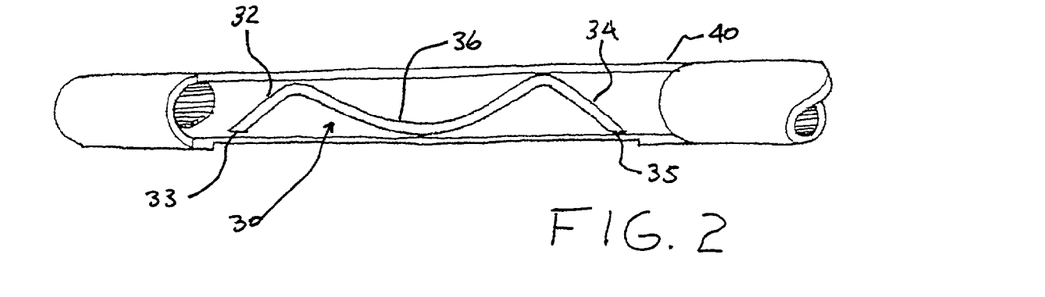
FIG. 2 is a side plan view of a staple device embodying the present invention shown in an initial stressed and distorted configuration within a deployment catheter.

FIG. 2 shows a mitral valve therapy staple device 30 embodying the present invention. The device 30 is shown confined within a deployment catheter 40 which will be described subsequently. The device 30 includes first and second tissue piercing leg portions 32 and 34 and a connection portion 36 between the leg portions 32 and 34. The leg portions 32 and 34 terminate in tissue piercing ends 33 and 35, respectively.

The device 30 is confined within the catheter 40 in a first or initial configuration. The initial configuration is exhibited by the connecting member 36 having a first arcuate or arched configuration, as illustrated, with the tissue piercing ends 33 and 35 pointing away from each other.

Figure 3:
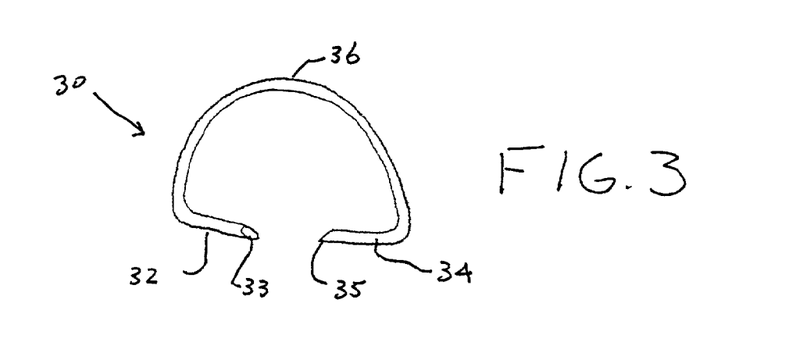
FIG. 3 is a side plan view of the staple device of FIG. 2 shown in a final unstressed and undistorted configuration.

The device 30 is formed of a material having shape memory so that once deployed, the connection portion 36 assumes a second or final configuration to be described with respect to FIG. 3 wherein the connection portion assumes a second arched configuration which is arched in a direction opposite than the first arched configuration illustrated in FIG. 2. To that end, the device 30 may be formed of, for example, Nitinol, a material well known for shape memory characteristics. Other suitable materials may include stainless steel or biocompatible plastic materials. Preferably, the connection portion 36 and leg portions 32 and 34 are formed of the same material stock as, for example, from a strip of Nitinol.

When the staple device 30 is deployed in the heart, the device 30 assumes its final configuration illustrated in FIG. 3. Here it may be seen that the connection member 36 has assumed an arched configuration opposite than that shown in FIG. 2 The final configuration of the connection member 36 causes the leg portions 32 and 34 to be more closely spaced together. In addition, in accordance with this preferred embodiment, when the device 30 is in its final configuration, the tissue piercing ends 33 and 35 point towards each other.

Figure 4:
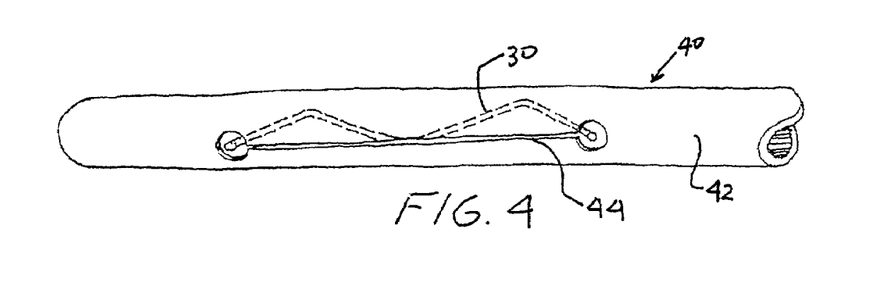
FIG. 4 is a side view of the deployment catheter illustrating a slot portion through which the staple device may be forced for deployment.
Figure 5:
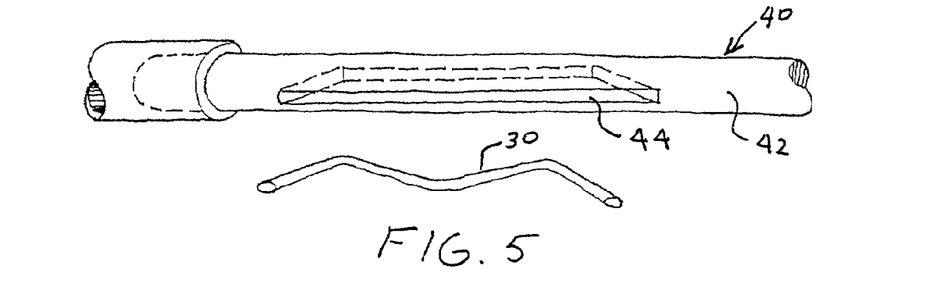
FIG. 5 is a side view illustrating the staple after being forced through the slot portion of the catheter.

Referring now to FIGS. 4 and 5, they illustrate the deployment catheter 40 in greater detail. Here it may be seen that the deployment catheter 40 includes a tubular wall 42 in which a slot 44 is formed. The staple device 30 is positioned adjacent the slot 44 to permit the staple device 30 to be forced through the tubular sidewall 42 and more particularly through the slot 44 for deployment in the heart. The slot 44 preferably comprises a reduced thickness of the tubular wall 42 to provide an effective seal prior to deployment but permitting a relatively modest force to urge the device 30 through the slot 44 and into the mitral valve annulus as will be described hereinafter. Hence, the slot 44 is a break-away slot providing seal integrity prior to deployment but permitting the staple 30 to be forced through the tubular wall 42 of the catheter 40 into the heart.

Figure 6:
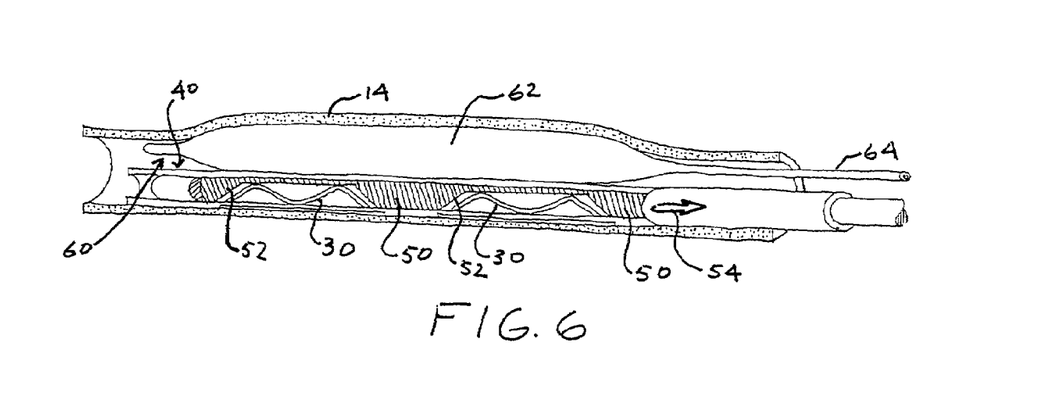
FIG. 6 is a side view of an assembly embodying the present invention shown within a coronary sinus and ready for deployment of a plurality of staple devices in accordance with the present invention.

FIG. 6 is a side view showing the catheter 40 within the coronary sinus 14. Also illustrated in FIG. 6 is a tool 50 which may be utilized for forcing the staples 30 through the tubular wall 42 of the catheter 40. Also shown in FIG. 6 is an urging member 60 which urges the catheter 40 against the wall of the coronary sinus adjacent the mitral valve annulus.

More specifically, the tool 50 includes a surface contour 52 which corresponds to the contour of the staple devices 30 when in the initial configuration. Displacement of the tool 50 in a proximal direction as indicated by the arrow 54 causes the tool 50 to urge or force the staple devices 30 through the tubular wall 42 of the catheter 40. As noted in FIG. 6, the plurality of staple devices 30 are urged or forced through the tubular wall 42 for deployment substantially simultaneously.

The urging member 60 preferably takes the form of an inflatable balloon 62. Preferably, the inflatable balloon 62 is inflatable by a conduit 64 and is carried by the catheter 40. Prior to deployment of the staple devices 30, the catheter 40 is placed in the coronary sinus adjacent the mitral valve annulus with the balloon 62 deflated. Thereafter, the balloon 62 is inflated so as to urge the catheter 40 against the wall of the coronary sinus adjacent the mitral valve annulus as illustrated. Thereafter, the tool 50 may be displaced proximally to urge or force the staple devices 30 through the tubular wall 42 of the catheter 40 for deployment.

Figure 7:
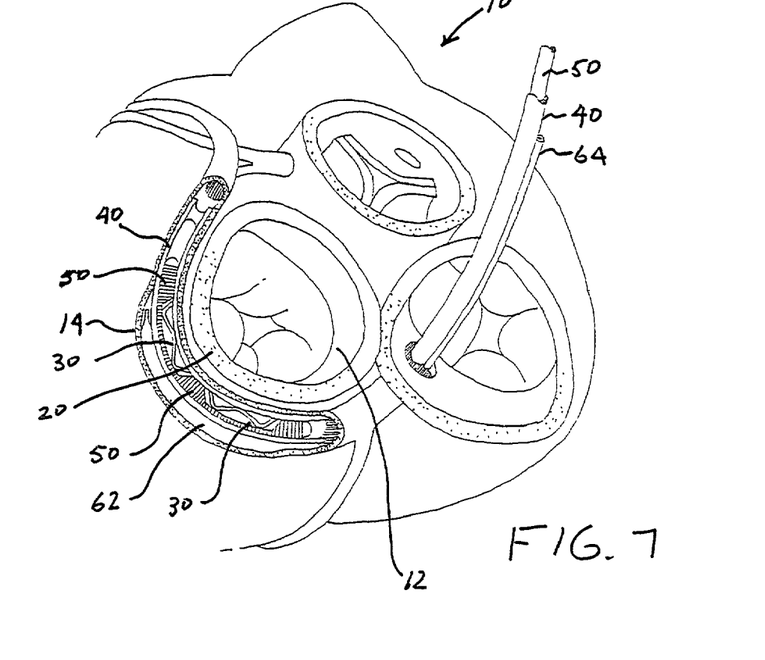
FIG. 7 is a superior view of a human heart similar to FIG. 1 illustrating a first step in the deployment of mitral valve staple devices embodying the present invention.
Figure 8:
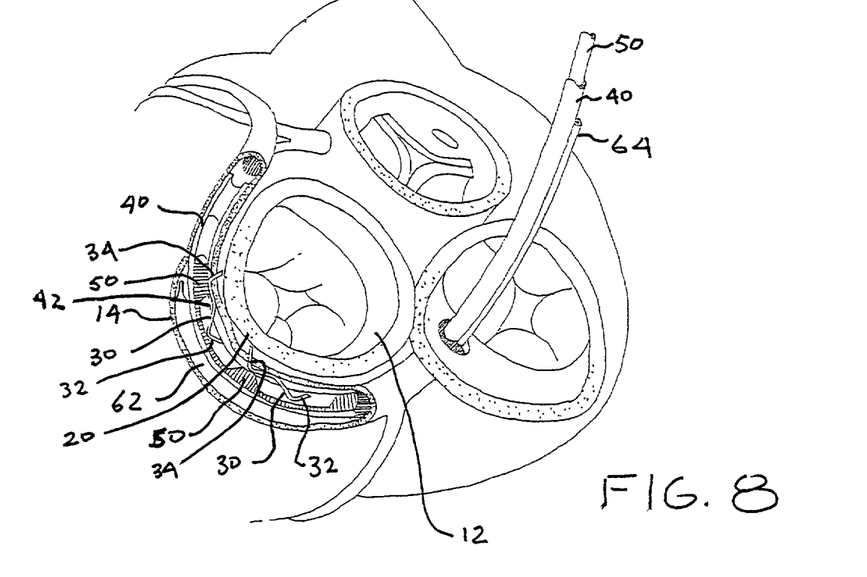
FIG. 8 is a view similar to FIG. 7 illustrating a further step in the deployment of the staple devices.

The deployment of the staple devices 30 is shown more particularly in FIGS. 7 and 8. In FIG. 7, it can be seen that the catheter 40 is positioned within the coronary sinus 14 adjacent to the mitral valve annulus 20. The balloon 62 has been inflated so as to urge the catheter 40 against the wall of the coronary sinus 14 which is adjacent the mitral valve annulus 20. The assembly is now ready to deploy the mitral valve staple devices 30.

Referring now to FIG. 8, it will be noted that the tool 50 is being displaced proximally and is forcing the staple devices 30 through the tubular wall 42 of the catheter 40. The leg portions are extending through the wall of the coronary sinus into the mitral valve annulus 20 or at least near to the annulus. Once the mitral valve staple devices 30 have been forced through the catheter sidewall with the leg portions piercing the mitral valve annulus, the staple devices will assume their final configuration. This is shown more particularly in FIG. 9.

Figure 9:
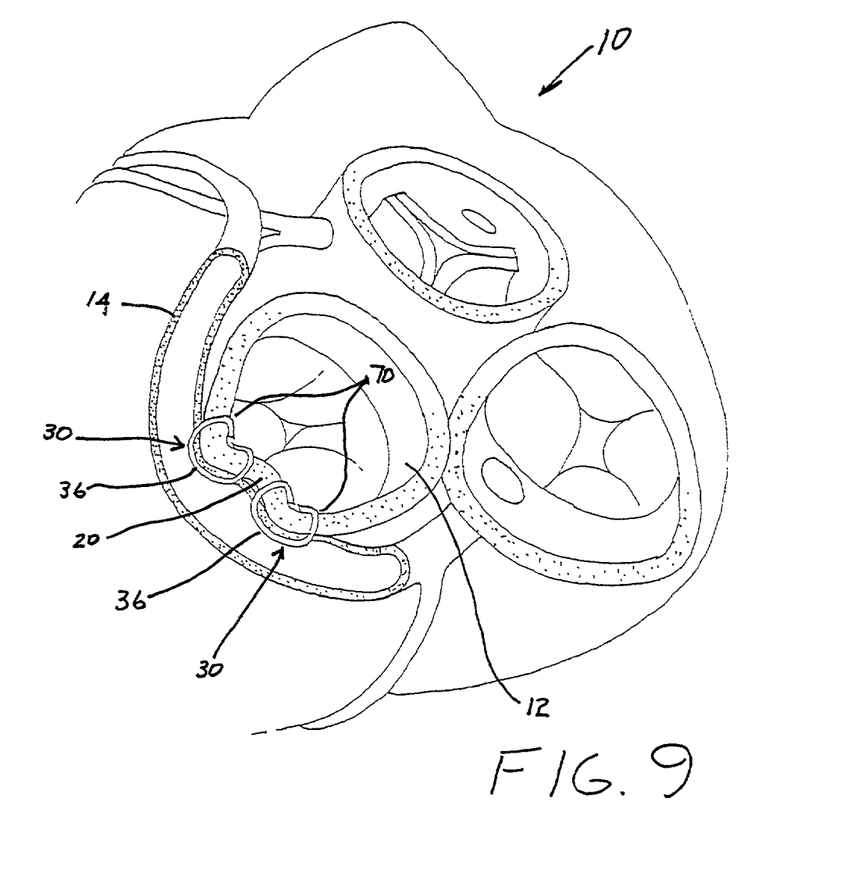
FIG. 9 is a superior view of a human heart similar to FIG. 7 illustrating the mitral valve staple devices deployed in the heart.

In FIG. 9, it can be seen that the connection portions 36 of the mitral valve staple devices 30 have assumed their final configuration. During the process of transitioning from the initial configuration to the final configuration, the tissue piercing leg portions have gathered-up mitral valve annulus tissue to tighten the mitral valve annulus. More specifically, as will be noted in FIG. 9, the radius of curvature of the mitral valve annulus 20 in a portion designated 70 has been dramatically increased. This tightening up of the mitral valve annulus will promote more efficient mitral valve action and advantageously terminate mitral regurgitation. While the tissue piercing leg portions are illustrated as piercing entirely through the mitral valve annulus, it will be appreciated by those skilled in the art that the mitral valve annulus wall need not necessarily be pierced entirely through and that the tissue piercing leg portions need only pierce into the mitral valve annulus.

While particular embodiments of the present invention have been shown and described, modifications may be made, and it is therefore intended in the appended claims to cover all such changes and modifications which fall within the true spirit and scope of the invention as defined by the claims.

The invention claimed is:

1. A device for effecting mitral valve annulus geometry of a heart, the device comprising: first and second leg portions, each leg portion terminating in a tissue piercing end; and a connection portion extending between the first and second leg portions, the connection portion having an initial stressed and distorted configuration to separate the first and second leg portions by a first distance when the tissue piercing ends pierce the mitral valve annulus and a final unstressed and undistorted configuration after the tissue piercing ends pierce the mitral valve annulus to separate the first and second leg portions by a second distance, the second distance being shorter than the first distance, wherein the initial configuration of the connection portion is a first arched configuration and the final configuration of the connection portion is a second arched configuration, the second arched configuration being arched in a direction opposite the first arched configuration.

2. The device of claim 1 wherein, when the connection portion is in the second arched configuration, the tissue piercing ends of the leg portions point toward each other.

3. A device for effecting mitral valve annulus geometry of a heart, the device comprising: first and second leg portions, each leg portion terminating in a tissue piercing end; and a connection portion extending between the first and second leg portions, the connection portion having an initial stressed and distorted configuration to separate the first and second leg portions by a first distance when the tissue piercing ends pierce the mitral valve annulus and a final unstressed and undistorted configuration after the tissue piercing ends pierce the mitral valve annulus to separate the first and second leg portions by a second distance, the second distance being shorter than the first distance, wherein the tissue piercing ends of the first and second leg portions point away from each other when the connection portion is in the initial configuration and wherein the tissue piercing ends of the first and second leg portions point toward each other when the connection portion is in the final configuration.

4. An assembly for effecting mitral valve annulus geometry of a heart, the assembly comprising: an elongated catheter being placeable in the coronary sinus of the heart adjacent the mitral valve annulus; at least one staple carried within the catheter, the at least one staple including first and second leg portions, each leg portion terminating in a tissue piercing end, and a connection portion extending between the first and second leg portions, the connection portion having an initial stressed and distorted configuration to separate the first and second leg portions by a first distance when the tissue piercing ends pierce the initial valve annulus and a final unstressed and undistorted configuration after the tissue piercing ends pierce the mitral valve annulus to separate the first and second leg portions by a second distance, the second distance being shorter than the first distance; and a tool that forces the at least one staple from the catheter to cause the tissue piercing ends of the first and second leg portions of the at least one staple to pierce the mitral valve annulus with the connection portion of the at least one staple in the initial configuration.

5. The assembly of claim 4 wherein the catheter includes a tubular wall and wherein the tool forces the at least one staple through the tubular wall of the catheter.

6. The assembly of claim 5 wherein the tubular wall includes a break-away slot adjacent the at least one staple that permits the at least one staple to be forced therethrough.

7. The assembly of claim 4 wherein the at least one staple comprises a plurality of staples.

8. The assembly of claim 7 wherein the catheter includes a tubular wall having a plurality of break-away slots, each slot being adjacent to a respective given one of the staples, that permit the staples to be forced through the tubular wall of the catheter and into the mitral valve annulus.

9. The assembly of claim 7 wherein the tool is configured to force the staples from the catheter substantially simultaneously.

10. The assembly of claim 4 further comprising an urging member that urges the catheter along and against a wall of the coronary sinus adjacent to the mitral valve annulus.

11. The assembly of claim 10 wherein the urging member is an elongated balloon.

12. The assembly of claim 10 wherein the urging member is carried by the catheter.

13. The assembly of claim 4 wherein the initial configuration of the connection portion of the at least one staple is a first arched configuration and the final configuration of the connection portion of the at least one staple is a second arched configuration, the second arched configuration being arched in a direction opposite the first arched configuration.

14. The assembly of claim 13 wherein, when the connection portion of the at least one staple is in the second arched configuration, the tissue piercing ends of the leg portions point toward each other.

15. The assembly of claim 4 wherein the leg portions and connection portion of the at least one staple are formed of the same material stock.

16. The assembly of claim 15 wherein the leg portions and the connection portion of the at least one staple are formed from Nitinol.

17. The assembly of claim 4 wherein the tissue piercing ends of the first and second leg portions of the at least one staple point away from each other when the connection portion is in the initial configuration and wherein the tissue piercing ends of the first and second leg portions of the at least one staple point toward each other when the connection portion is in the final configuration.

18. A method of effecting mitral valve annulus geometry of a heart, the method including the steps of: providing at least one staple including first and second leg portions, each leg portion terminating in a tissue piercing end, and a connection portion extending between the first and second leg portions, the connection portion having an initial stressed and distorted configuration to separate the first and second leg portions by a first distance when the tissue piercing ends pierce the mitral valve annulus and a final unstressed and undistorted configuration after the tissue piercing ends pierce the mitral valve annulus to separate the first and second leg portions by a second distance; the second distance being shorter than the first distance; placing the at least one staple into a catheter; locating the catheter in the coronary sinus of the heart so that the at least one staple is adjacent the mitral valve annulus; and releasing the at least one staple from the catheter to cause the tissue piercing ends of the first and second leg portions of the at least one staple to pierce the mitral valve annulus with the connection portion of the at least one staple in the initial configuration.

19. The method of claim 18 wherein the catheter includes a tubular wall and wherein the releasing step includes the step of forcing the at least one staple through the tubular wall of the catheter.

20. The method of claim 19 wherein the tubular wall includes a break-away slot adjacent the at least one staple and wherein the releasing step includes forcing the at least one staple therethrough the break-away slot.

21. The method of claim 18 wherein the at least one staple comprises a plurality of staples.

22. The method of claim 21 wherein the catheter includes a tubular wall having a plurality of break-away slots, each slot being adjacent to a respective given one of the staples, and wherein the releasing step includes the step of forcing the staples through the break-away slots of the tubular wall of the catheter and into the mitral valve annulus.

23. The method of claim 21 wherein the plurality of staples are forced from the catheter substantially simultaneously.

24. The method of claim 18 further including the step of urging the catheter along and against a wall of the coronary sinus adjacent to the mitral valve annulus prior to the releasing step.

25. The method of claim 24 wherein the urging step includes placing an urging member in the catheter.

26. The method of claim 25 wherein the urging member is secured within the catheter.

27. The method of claim 25 wherein the urging step includes the steps of providing an elongated balloon within the catheter and inflating the elongated balloon.

28. An assembly for effecting mitral valve annulus geometry of a heart, the assembly comprising: an elongated catheter being placeable in the coronary sinus of the heart adjacent the mitral valve annulus; at least one staple carried within the catheter, the at least one staple including first and second tissue piercing portions, each tissue piercing portion terminating in a tissue piercing end, and a connection portion extending between the first and second tissue piercing portions, the connection portion having an initial stressed and distorted configuration to separate the first and second tissue piercing portions by a first distance when the tissue piercing ends pierce the mitral valve annulus and a final unstressed and undistorted configuration after the tissue piercing ends pierce the mitral valve annulus to separate the first and second tissue piercing portions by a second distance, the second distance being shorter than the first distance; and a tool that forces the at least one staple from the catheter to cause the tissue piercing ends of the first and second tissue piercing portions of the at least one staple to pierce the mitral valve annulus with the connection portion of the at least one staple in the initial configuration.

29. An assembly for effecting tissue geometry of an organ, the assembly comprising: an elongated catheter being placeable in a vessel of the body adjacent the tissue to be effected; at least one staple carried within the catheter, the at least one staple including first and second leg portions, each leg portion terminating in a tissue piercing end, and a connection portion extending between the first and second leg portions, the connection portion having an initial stressed and distorted configuration to separate the first and second leg portions by a first distance when the tissue piercing ends pierce the tissue and a final unstressed and undistorted configuration after the tissue piercing ends pierce the tissue to separate the first and second leg portions by a second distance, the second distance being shorter than the first distance; and a tool that forces the at least one staple from the catheter to cause the tissue piercing ends of the first and second leg portions of the at least one staple to pierce the tissue with the connection portion of the at least one staple in the initial configuration.

30. A method of effecting tissue geometry of an organ, the method including the steps of: providing at least one staple including first and second tissue piercing portions, each tissue piercing portion terminating in a tissue piercing end, and a connection portion extending between the first and second tissue piercing portions, the connection portion having an initial stressed and distorted configuration to separate the first and second tissue piercing portions by a first distance when the tissue piercing ends pierce the tissue and a final unstressed and undistorted configuration alter the tissue piercing ends pierce the tissue to separate the first and second tissue piercing portions by a second distance, the second distance being shorter than the first distance; placing the at least one staple into a catheter; locating the catheter in a vessel of the body so that the at least one staple is adjacent the tissue to be effected; and releasing the at least one staple from the catheter to cause the tissue piercing ends of the first and second tissue piercing portions of the at least one staple to pierce the tissue to be effected with the connection portion of the at least one staple in the initial configuration.

* * * * *